(12) United States Patent
Nahon

(10) Patent No.: US 6,319,248 B1
(45) Date of Patent: Nov. 20, 2001

(54) SPRAY CATHETER

(75) Inventor: Daniel Nahon, Ottawa (CA)

(73) Assignee: CryoCath Technologies, Inc., Kirkland (CA)

( * ) Notice: Subject to any disclaimer, the term of this patent is extended or adjusted under 35 U.S.C. 154(b) by 0 days.

(21) Appl. No.: 09/124,611

(22) Filed: Jul. 29, 1998

(51) Int. Cl.[7] .................................................. A61B 18/18
(52) U.S. Cl. ............................................ 606/22; 604/523
(58) Field of Search .................................... 604/113, 114, 604/264, 523, 22, 23, 20–21, 93.01; 607/96; 606/20–23, 25–26

(56) References Cited

U.S. PATENT DOCUMENTS

| | | | |
|---|---|---|---|
| 3,651,813 | 3/1972 | Byrne | 128/303.1 |
| 3,712,306 | 1/1973 | Byrne | 128/303.1 |
| 3,889,681 | 6/1975 | Waller et al. | 128/303.1 |
| 4,043,341 | 8/1977 | Tromovitch | 128/303.1 |
| 4,082,096 | 4/1978 | Benson | 128/303.1 |
| 4,900,303 * | 2/1990 | Lemelson | 604/54 |
| 5,078,713 | 1/1992 | Varney | 606/23 |
| 5,098,428 | 3/1992 | Sandlin et al. | 606/22 |
| 5,108,390 | 4/1992 | Potocky et al. | 606/21 |
| 5,139,496 | 8/1992 | Hed | 606/23 |
| 5,147,355 | 9/1992 | Friedman et al. | 606/23 |
| 5,254,116 | 10/1993 | Baust et al. | 606/23 |
| 5,281,215 | 1/1994 | Milder | 606/20 |
| 5,498,239 * | 3/1996 | Galel et al. | 604/95 |
| 5,588,432 * | 12/1996 | Crowley | 128/660.3 |
| 5,738,682 | 4/1998 | Jensma | 606/23 |
| 5,830,179 * | 11/1998 | Mikus et al. | 604/49 |
| 5,846,235 * | 12/1998 | Pasricha et al. | 606/23 |
| 5,899,898 * | 5/1999 | Arless et al. | 606/22 |
| 5,964,223 * | 10/1999 | Baran . | |
| 6,027,499 * | 2/2000 | Johnston et al. . | |

* cited by examiner

Primary Examiner—Sharon Kennedy
Assistant Examiner—Catherine Serke
(74) Attorney, Agent, or Firm—Gunster, Yoakley & Stewart, P.A.

(57) ABSTRACT

A spray catheter includes a flexible member having a spray tip and a fluid path through the flexible member to the spray tip. The catheter can be deformable and may include a mechanism for varying the spray geometry of the spray tip.

14 Claims, 4 Drawing Sheets

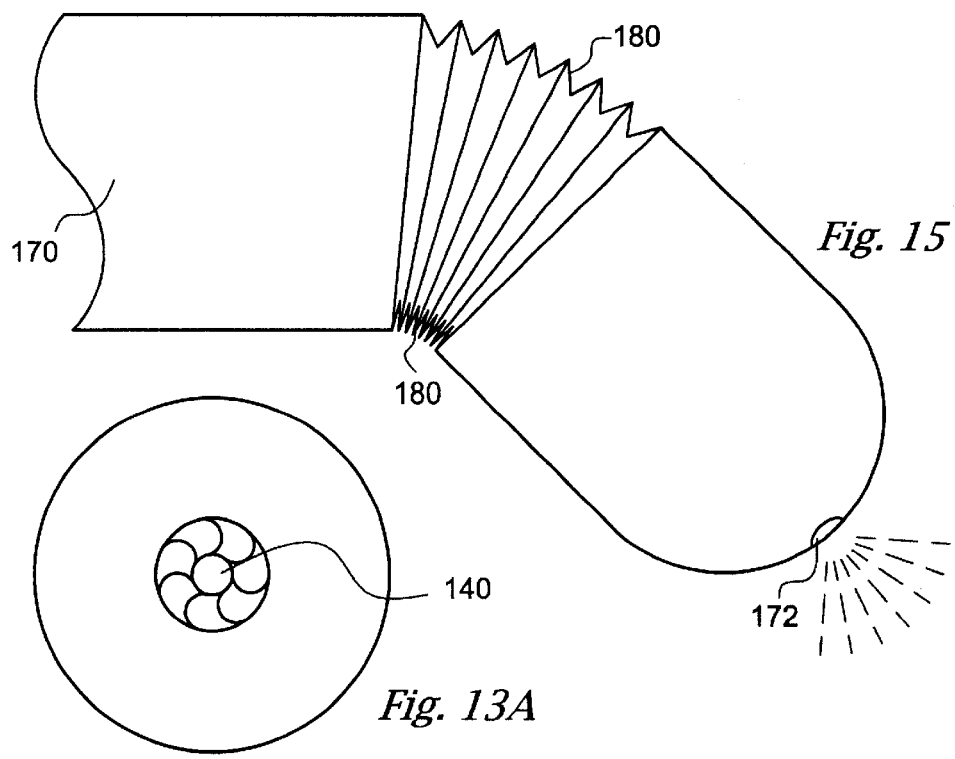
*Fig. 15*
*Fig. 13A*
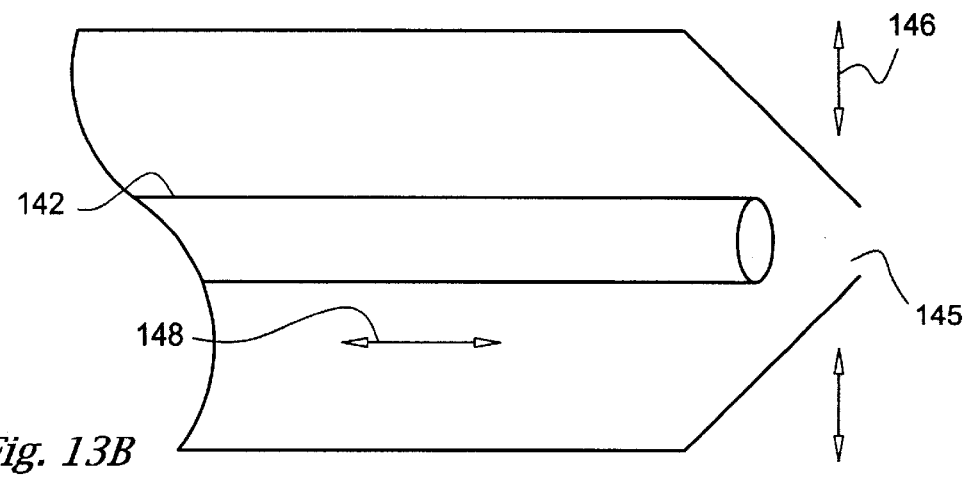
*Fig. 13B*
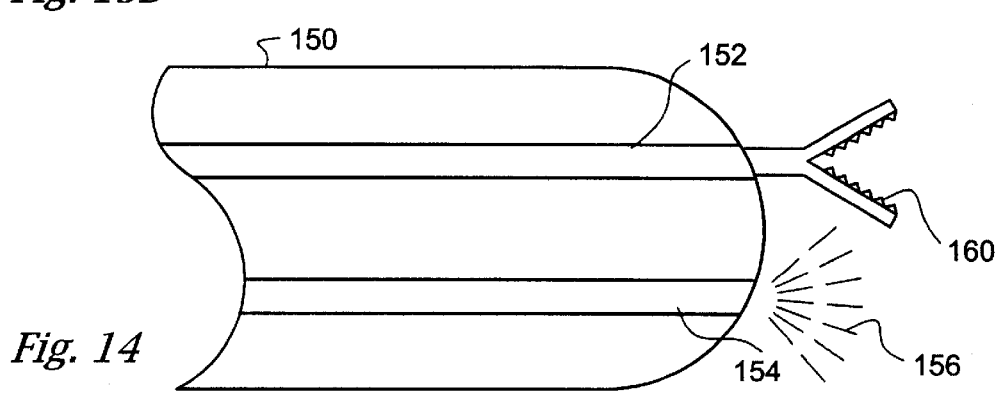
*Fig. 14*

SPRAY CATHETER

CROSS-REFERENCE TO RELATED APPLICATIONS

Not applicable.

STATEMENTS REGARDING FEDERALLY SPONSORED RESEARCH

Not applicable.

FIELD OF THE INVENTION

The invention relates to medical devices, and more particularly to minimally invasive surgical devices.

BACKGROUND OF THE INVENTION

Cold fluid such as liquified nitrogen, can be topically applied to living tissue or growths thereon to freeze or ablate an area of tissue. However, topical application of coolant is typically only suitable for easily accessible areas of the body, such as the skin where the application of the fluid is commonly performed with a cotton swab.

Recent advances in the cryosurgical arts provide for the use of rigid applicators such as probes, through which a cool fluid circulates and wherein the outside wall of the probe is applied directly to a treatment site. However, it is difficult, if not impossible to apply a rigid applicator to the entirety of an irregular surface. Other prior art topical applicators such as the type having large "oil can" type coolant containers may provide better overall coverage than a cold probe but these "oil can" types by virtue of their size and rigidity, provide limited accessibility to subcutaneous regions of the body.

It would be desirable to have a device which could be utilized with current minimally invasive techniques to apply a coolant to internal tissues surfaces.

BRIEF SUMMARY OF THE INVENTION

The present invention overcomes the shortcomings of the prior art by providing a spray catheter adapted for minimally invasive application that is particularly well suited for treating large and/or irregular surface areas. The spray catheter includes a flexible catheter member with a spray tip, the flexible catheter member having a cryogenic fluid path through the flexible member to the spray tip.

The spray catheter of the invention can be a component in a cryogenic system that further includes a cryogenic fluid supply in communication with the spray catheter, and an integrated fluid controller for regulating the flow of the cryogenic fluid into the spray catheter. The cryogenic fluid can be a gas, a liquid, a liquified gas or a combination of these and is preferably a biocompatible refrigerant such as carbon dioxide, nitrous oxide, liquid nitrogen or a combination of different gases.

The spray catheter would be able perform varying size ablations on both uniform and irregular tissue surfaces. The spray catheter would be appropriately used in areas of the body where the release of coolant is not contraindicated.

BRIEF DESCRIPTION OF THE DRAWINGS

A more complete understanding of the present invention and the attendant advantages and features thereof will be more readily understood by reference to the following detailed description when considered in conjunction with the accompanying drawings wherein:

FIG. 13A illustrates a variable geometry spray mechanism;

FIG. 13B illustrates another variable geometry spray mechanism;

FIG. 14 illustrates an embodiment of the spray tip catheter incorporating a biopsy mechanism; and FIG. 15 illustrates yet another embodiment of the spray tip catheter.

DETAILED DESCRIPTION OF THE INVENTION

Figure 1:
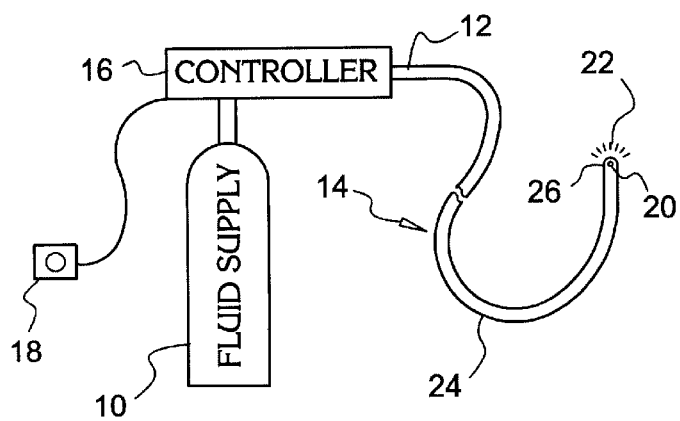
FIG. 1 is a schematic illustration of an embodiment of a cryosurgical system in accordance with the invention.

FIG. 1 is a schematic illustration of a cryosurgical system in accordance with the invention. The system includes a supply of cryogenic or cooling fluid 10 in communication with the proximal end 12 of a catheter 14. In an exemplary embodiment, the supply 10 may be a canister or removable cartridge to allow for ease of portability and maintenance. The catheter 14 is made up of an elongate flexible member 24 and a spray tip 26 disposed proximate a distal end 22 of the catheter 14. A fluid controller 16 is integrated with the catheter 14 for regulating the flow of cryogenic fluid into the catheter in response to a controller command.

Controller commands can include programmed instructions, sensor signals, and manual user input. For example, the fluid controller 16 can be programmed or configured to increase and decrease the pressure of the fluid by predetermined pressure increments over predetermined time intervals. In another exemplary embodiment, the fluid controller 16 can be responsive to input from a control device 18 to permit flow of the cryogenic fluid into the catheter 14. The spray tip 26 may be selectively adapted for either air assisted or purely hydraulic spray operating modes and includes actuating means such as the control device 18 for controlling operation of the spray tip 26 without the necessity for complicated or cumbersome connecting cables.

In one embodiment, the system as described herein is adapted for hand-held use. In such a configuration, the system would include an integrated controller, a control device such as a finger-actuated trigger and a portable fluid supply such as a removable cartridge.

One or more temperature sensors 20 in electrical communication with the controller 16 can be provided to monitor, regulate or terminate the flow of cryogenic fluid into the catheter 14 when a predetermined temperature at a selected point or points on or proximal to the catheter is/are obtained. For example, a temperature sensor 20 can be placed at a point proximate the distal end 22 of the catheter 14 and other temperature sensors 20 can be placed at spaced intervals between the distal end of the catheter and another point that is between the distal end and the proximal end.

Figure 2:
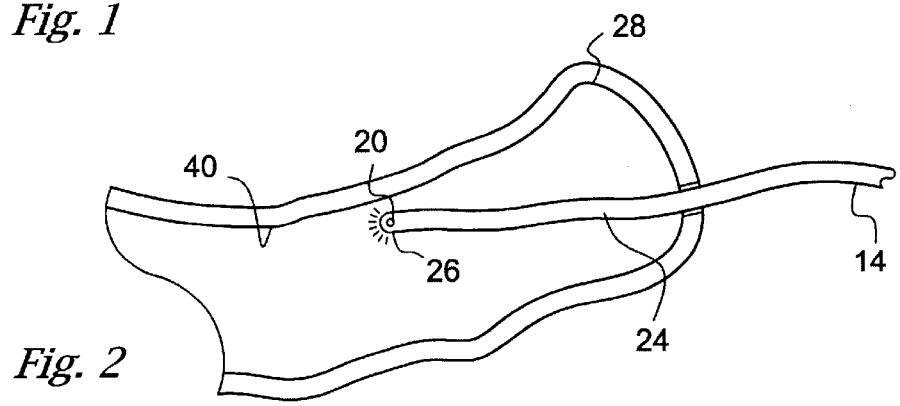
FIG. 2 is a sectional view showing placement of the spray tip catheter of FIG. 1.
Figure 3:
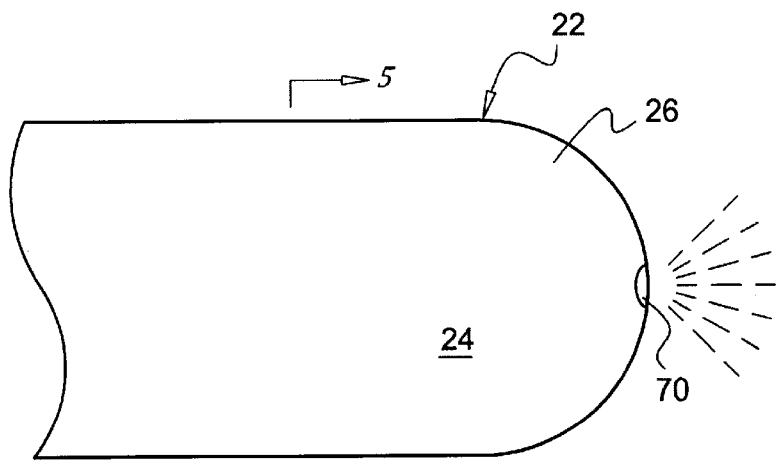
FIG. 3 illustrates one embodiment of the spray tip catheter in accordance with the invention.
Figure 4:
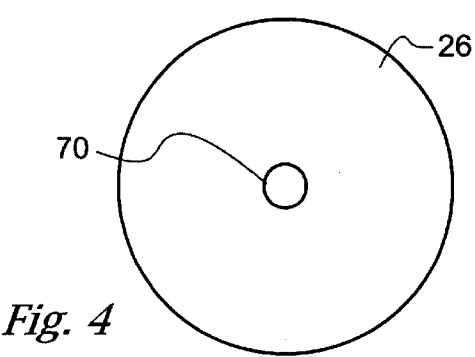
FIG. 4 is a front view of the spray tip catheter of FIG. 3.

The cryogenic system of FIG. 1 is better understood with reference to its use in an operative procedure as shown in FIG. 2. Due to the nature of the spraying mechanism, the catheter is best suited for procedures where the operative site is open to the atmosphere such as gastrointestinal tract, uterus, esophagus, bronchus or open surgical field. Following the determination of a proposed operative site within, for example, a gastrointestinal tract 28, the catheter 14 is directed through an incision or natural body opening, such as the mouth or rectum, to a region 40 within the gastrointestinal tract 28 where the spray application will be made. The spray tip 26 is placed proximate to the tissue to be treated. The controller 16 allows or causes cryogenic fluid to flow from the cryogenic fluid supply 10 to the fluid path in the catheter 14 and thence to the spray tip 26 to cover the desired region 40. The coolant or fluid is then expelled from the spray lip 26 to treat the desired region 40 within the gastrointestinal tract 28.

Having described the function of the cryogenic catheter 14 and its use in a system context, several exemplary embodiments of the spray tip catheter are now described in greater detail. Each of the illustrated catheters includes a spray tip that provides for the discharge of cryogenic fluid. A[]s used herein the term "fluid" may refer to either a liquid, a gas, a liquified gas or a combination these. Exemplary fluids include any biocompatible refrigerant such as liquid nitrogen, nitrous oxide, carbon dioxide or any inert gas such as helium, argon, neon, etc. or any combination thereof.

Referring to FIGS. 3–6, the catheter 14 is made up of a flexible member 24 having a spray tip 26 positioned proximate the distal end 22 of the catheter 14. The catheter 14 includes an internal fluid path which runs from the proximal end 12 of the catheter 14 through to the spray tip 26 at the distal end 22. Although described in greater detail below, exemplary fluid paths can be one or more channels defined externally by the flexible member 24, and/or by one or more additional flexible members that are internal to the flexible member 24.

In exemplary embodiments of the invention, the flexible member 24 of the catheter 14 is deformable and steerable. An exemplary deformation is from a linear configuration to an arcuate configuration and is accomplished using mechanical and/or electrical devices known to those skilled in the art. For example, a wall portion of the flexible member 24 can include a metal braid, not shown, to make the catheter torqueable for overall catheter steering and placement. Additionally, a cord, wire or cable can be incorporated with, or inserted into, the catheter for steering of the catheter to the desired application area.

As used herein, "flexible" can be defined in functional terms. For example, embodiments of the device can be sufficiently flexible and narrow to be inserted into non-linear body passages or working channels of endoscopes less than 10 mm in diameter. Exemplary embodiments can have a length ranging from 10 cm to 200 cm and an external diameter ranging from 1 mm to 10 mm in diameter.

In the embodiment illustrated in FIGS. 3–8, the spray tip 26 has a single central opening 70 disposed at the distal end 22 of the catheter 14. Generally, the size of the opening will have a diameter in the range of about 0.01 mm to 3.0 mm. The dimensions of the opening will vary depending on the desired spray application and required spray area.

Figure 5:
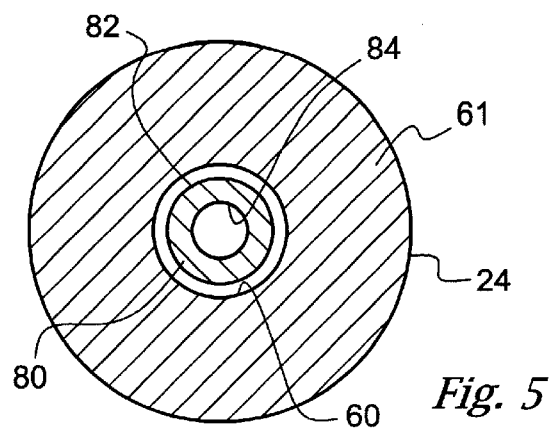
FIG. 5 is a sectional view of the spray tip catheter of FIG. 3.

In an exemplary embodiment, the spray tip opening is substantially circular to provide a generally circular spray pattern. In other embodiments, the opening can be of different shapes to provide correspondingly different spray patterns or geometries. For example, in another embodiment, the opening can be hemispherical to provide a correspondingly hemispherical spray pattern. Alternatively the opening 70 can have a variable geometry controlled by the operator via a mechanical and/or electrical mechanism which will vary the spray pattern via a variable geometry opening as discussed in more detail later herein, As shown in FIG. 5, the flexible member 24 of the catheter further includes an inner wall surface 60 that defines an internal passageway in the catheter 14. An internal conduit or lumen 80 is further disposed within the flexible member 24. The internal lumen 80 further includes an outer wall surface 82 and an inner wall surface 84. The inner wall surface 84 defines a conduit or flow path for the passage of cryogenic fluid. In another exemplary embodiment, the inner wall surface 60 of the catheter 14 defines the flow path provided that the inner wall 61 is made of an insulating material to prevent excess thermal loss through the catheter 14.

Figure 6:
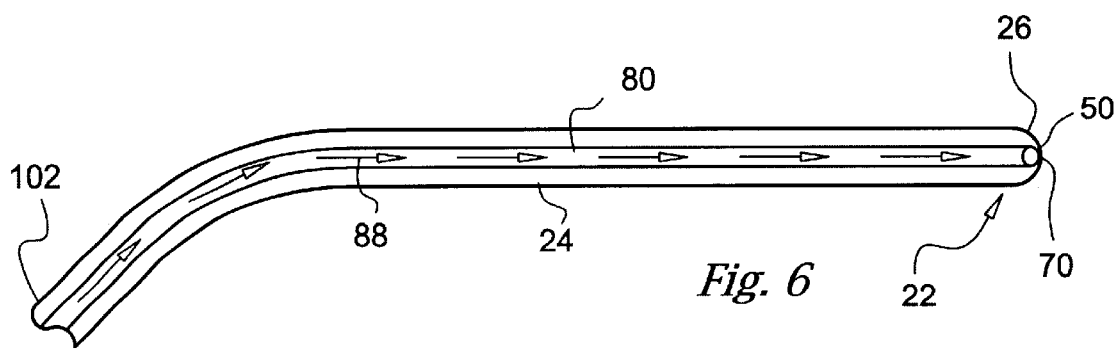
FIG. 6 illustrates a flow path for the spray tip catheter of FIG. 3.

As shown in FIGS. 5 and 6, the cryogenic fluid travels within the internal lumen 80 and the fluid is discharged from a fluid exit defined by the opening 70 at the distal end 22 of the flexible member 24. The diameter of the internal lumen 80 is dependent upon a number of factors, including the diameter of the spray tip opening and the desired pressure required for the cryogenic fluid. The internal lumen may be a separate tube within a larger outer tube or alternatively it may simply be a passageway formed within a solid tube. When configured as a separate tube within a larger tube, the inner tube may be glued, held mechanically such as with screws or it could be held in an interference fit to communicate with opening 70.

Referring again to FIGS. 5 and 6, the catheter is illustrated having a second or internal lumen 80 concentric within a first or outer flexible member 24, wherein the inner flexible lumen 80 defines a fluid path to the spray tip 26. The inner lumen 80 communicates with the single central opening 70 disposed on the spray tip 26. Cryogenic fluid is expelled from the opening 70 and is exhausted out the distal end of the catheter 14 along a fluid path defined by the outer wall 84 of the inner lumen 80 and the inner wall surface 60 of the flexible member 24.

Referring to FIG. 6, in an exemplary embodiment of the spray tip catheter, the catheter 14 has a fluid inlet at a rearward end 102 of the flexible member 24 and pressurized fluid can be directed in a straight longitudinal flow path, as shown by arrows 88, through an internal passageway such as the internal lumen 80 which can be a plastic tube. The internal lumen 80 is a fluid conduit and it is responsive to actuation and deactuation of the actuating means, such as the control device 18. In this embodiment, the spray tip 26 has a fluid outlet at the forwardmost end 50 of the catheter 14.

Figure 7:
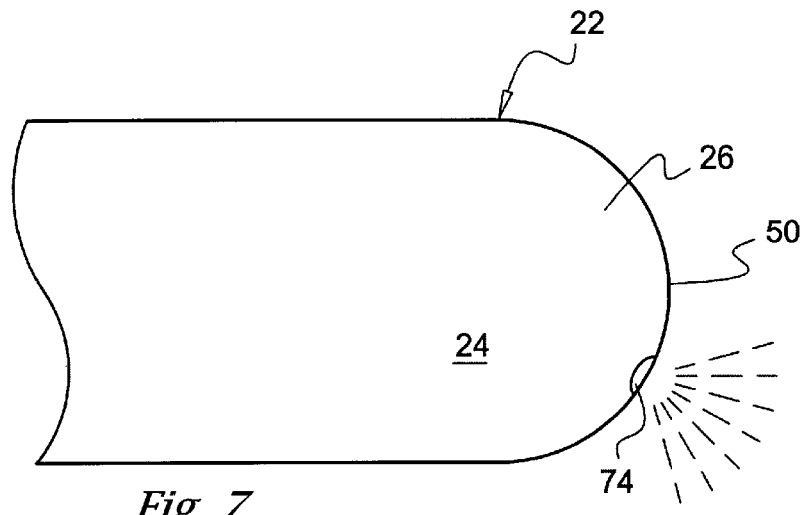
FIG. 7 illustrates yet another embodiment of the spray tip catheter.
Figure 8:
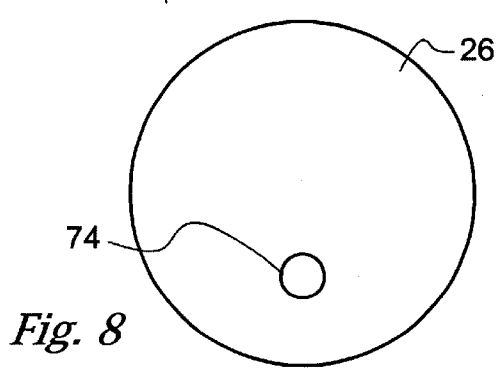
FIG. 8 is a front view of the spray tip catheter of FIG. 7.

Referring to FIGS. 7 and 8, a further embodiment of the spray tip catheter is shown. In this embodiment, the catheter includes a single off-center opening 74. The opening 74 is disposed proximate the distal end 22 of the catheter 14 and is adapted to provide an offset spray pattern relative to the forwardmost portion 50 of the spray tip 26. In this embodiment, a variety of different configurations and placements of the opening can be used depending on the required angle of spray application.

Figure 9:
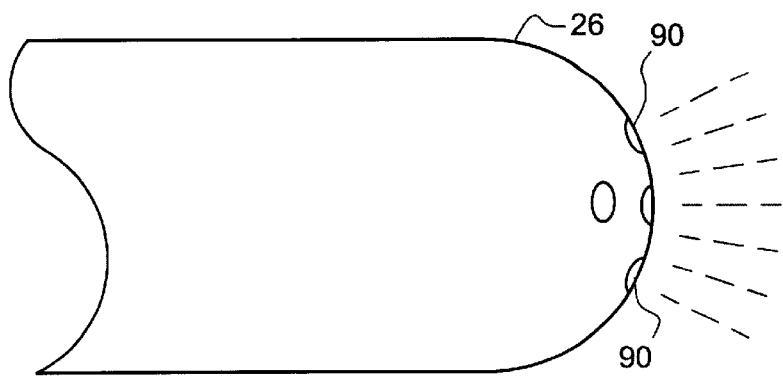
FIG. 9 illustrates yet another embodiment of the spray tip catheter.
Figure 10:
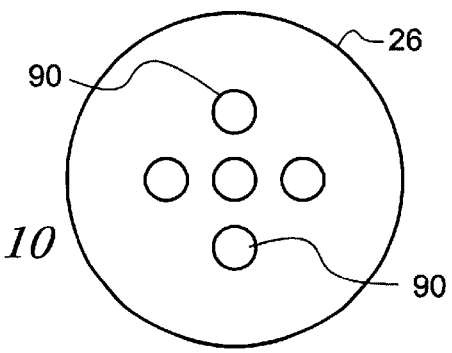
FIG. 10 is a front view of the spray tip catheter of FIG. 9.

Referring to FIGS. 9 and 10, a further embodiment of the spray tip catheter is shown. As shown in FIG. 10, the catheter can be provided with a plurality of openings 90 proximate the distal end 22 of the catheter 14. The plurality of openings 90 are arranged to achieve a more dispersed spreading of the coolant fluid across the entire application area. Although the openings are arranged in a substantially "cross-like" configuration, a variety of different configurations and numbers of openings can be used. For example, two, three, four or more than five openings may be used to provide correspondingly different spray geometries and patterns.

Figure 11:
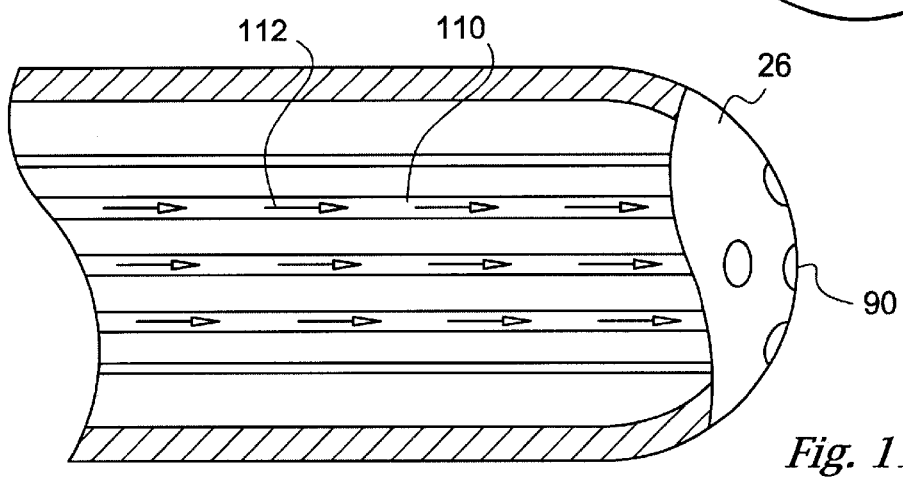
FIG. 11 illustrates a flow path of the spray tip catheter of FIG. 9.

In an exemplary embodiment of the spray tip catheter shown in FIG. 11, each opening of the spray tip 26 is connected to and communicates with a respective separate internal conduit or lumen 110. Each lumen 110 corresponds to a specific opening 90. In an exemplary embodiment, the multiple internal lumens are connected to the same cryogenic fluid supply and controller. In another embodiment, each separate lumen and corresponding opening on the spray tip can is provided with a separate and distinct fluid supply and controller. Accordingly, each internal lumen and opening can be selectively activated and deactivated to provide a variety of different spray geometries and patterns. For example, it is contemplated that for the multiple opening pattern shown in FIG. 10, for a specific operative procedure, the central opening could be shut off and the surrounding opening provided with a fluid supply to produce a spray pattern in the shape of a circle with minimal cryogenic fluid being applied in the center of the spray area.

Figure 12:
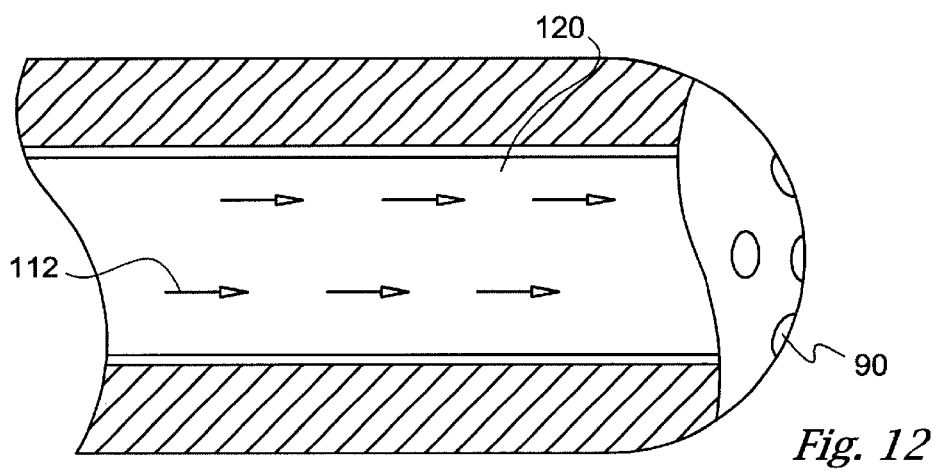
FIG. 12 illustrates an alternate flow path of the spray tip catheter of FIG. 9.

As shown in FIGS. 11 and 12, the fluid path is shown by arrows 112 wherein the fluid flows longitudinally through the catheter 14. In an alternate embodiment, as shown in FIG. 12, a single internal lumen 120 is connected to and communicates with the multiple openings and a single fluid path is provided to the multiple openings.

Referring to FIGS. 13A–13B, mechanisms for varying the spray geometry are shown. In an exemplary embodiment shown in FIG. 13A, the spray tip opening 140 is adjustable to vary the size of the spray application area using a plurality of overlapping fan-like members which when rotated, dimensionally expand or contract the spray tip opening 140. The mechanism can be mechanically or electrically adjusted as is known by those of ordinary skill in the art.

As shown in FIG. 13B, another embodiment for varying the spray geometry is shown. In this embodiment, the catheter includes an internal lumen 142 which can be variably adjusted longitudinally, as shown by arrow 148 relative to opening 145. The diameter of the opening 145 can also be adjusted, as shown by arrows 146. By varying either or both the position of the internal lumen 142 and the size of the opening 145, the spray geometry may be adjusted accordingly.

Referring to FIG. 14, a biopsy mechanism is shown incorporated into the spray tip catheter 150. The biopsy mechanism 160 resides within a first lumen or channel 152 and a second lumen 154 provides for delivery of the fluid to the spray tip 156.

A further embodiment of the spray tip catheter is shown in FIG. 15. In this embodiment, the catheter includes a spray tip 172 which can be tilted or angled relative to rest of a catheter member 170. The catheter member 170 can be angled and positioned by a series of folded or bellows-like structures 180. The bellows material can be sufficiently elastic to provide for increased flexibility but also can retain sufficient stiffness so that the angled position of the spray tip can be maintained. Deformation or bending of the spray tip can be accomplished by hand or by other means such as an internal guiding rod which can be mechanically or electrically manipulated to deform the spray tip region. In use, the catheter can be positioned proximate the desired application area and then the spray tip would be angled or pointed towards the application area before spraying.

A variety of modifications and variations of the present invention are possible in light of the above teachings. Specifically, many embodiments are illustrated that are adapted for insertion into any structure of the body, and can be introduced into the body directly through incisions or through structures such as trocars. Furthermore, although some of the illustrated devices are particularly well suited for gastrointestinal and pulmonary bronchoscopy procedures, the same embodiments and others are equally suited to other organs and/or any body portion that would benefit from the application of thermal energy such as the uterus and bronchus areas. Thus, the devices as shown are not to be limited to catheters but should be viewed more broadly as cryogenic structures or portions thereof. It is therefore understood that, within the scope of the appended claims, the present invention may be practiced otherwise than as specifically described hereinabove. All references cited herein are expressly incorporated by reference in their entirety.

What is claimed is:

1. A spray catheter comprising:

an elongate flexible member having a proximal and a distal end;

a spray tip formed at the distal end of the elongate flexible member, the spray tip having a centerpoint and a single opening, the opening being offset from the centerpoint of the spray tip; and a coolant fluid path through the elongate flexible member to the spray tip, wherein a coolant is flowed through the fluid path and expelled from the opening to provide a spray pattern offset from the centerpoint of the single opening.

2. The spray catheter of claim 1, wherein the opening has a diameter in the range of 0.01 to 0.25 mm.

3. The spray catheter of claim 1, wherein the flexible member includes an internal lumen in communication with the spray tip.

4. The spray catheter of claim 1, wherein the elongate member is deformable.

5. The spray catheter of claim 1, wherein the coolant is a biocompatible gas.

6. The spray catheter of claim 5, wherein the coolant is selected from the group consisting of nitrous oxide, carbon dioxide, helium, argon and neon.

7. A spray catheter, comprising:

an elongate flexible member having a proximal and a distal end;

a spray tip formed at the distal end of the elongate flexible member, the spray tip having an opening;

a first lumen disposed within the flexible member and in fluid communication with the opening to form a coolant fluid path, a second lumen disposed within the flexible member; and a biopsy channel formed at the distal end of the elongate flexible member and in communication with the second lumen of the flexible member, wherein a biopsy can be performed simultaneously with a cryo-treatment procedure.

8. A spray catheter, comprising:

an elongate flexible member having a proximal and a distal end;

a spray tip formed at the distal end of the elongate flexible;

a coolant fluid path through the elongate flexible member to the spray tip, wherein coolant is expelled from the spray tip; and means for varying a spray geometry of the spray tip, wherein the means for varying spray geometry includes a plurality of overlapping fan-like members.

9. The spray catheter of claim 8, wherein the means includes a plurality of selectively adjustable fan-like members.

10. A spray catheter, comprising:

an elongate flexible member having a proximal and a distal end and a plurality of lumens disposed within the flexible member, each of the plurality of lumens defining a separate coolant flow path from the proximal end of the flexible member to the distal end of the flexible member, a spray tip formed at the distal end of the elongate flexible member, the spray tip having a plurality of openings wherein each of the plurality of openings is in fluid communication with one of the plurality of lumens such that each of the openings forms a separate fluid outlet; and further comprising a coolant, wherein the coolant is passed through the coolant flow paths to control a cooling effect at the spray tip, wherein the coolant is a gas.

11. The spray catheter of claim 10, further comprising a biocompatible gas coolant.

12. The spray catheter of claim 10, wherein the coolant is selected from the group consisting of nitrous oxide, carbon dioxide, helium, argon and neon.

13. The spray catheter of claim 10, wherein the coolant is selected from the group consisting of nitrous oxide, carbon dioxide, helium, argon and neon.

14. The spray catheter of claim 10, further comprising means for varying a spray geometry of the spray tip.

* * * * *